US006351983B1

United States Patent
Haas et al.

(10) Patent No.: US 6,351,983 B1
(45) Date of Patent: Mar. 5, 2002

(54) PORTABLE GAS CHROMATOGRAPH MASS SPECTROMETER FOR ON-SITE CHEMICAL ANALYSES

(75) Inventors: Jeffrey S. Haas, San Ramon; John F. Bushman, Oakley; Douglas E. Howard, Livermore; James L. Wong, Livermore; Joel D. Eckels, Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/289,755

(22) Filed: Apr. 12, 1999

(51) Int. Cl.[7] .................................. G01N 30/02
(52) U.S. Cl. ........................ 73/23.37; 250/281
(58) Field of Search ................. 73/23.25, 23.37; 250/280, 281, 288, 291

(56) References Cited

U.S. PATENT DOCUMENTS

| | | | | |
|---|---|---|---|---|
| 5,051,557 A | * | 9/1991 | Satzger | 219/121.52 |
| 5,083,450 A | * | 1/1992 | Grindstaff | 73/23.25 |
| 5,155,357 A | * | 10/1992 | Hemond | 250/291 |
| 5,313,061 A | * | 5/1994 | Drew et al. | 250/281 |
| 5,426,300 A | * | 6/1995 | Voss et al. | 250/288 |
| 5,463,220 A | * | 10/1995 | Young et al. | 250/288 |
| 5,472,670 A | * | 12/1995 | Harrington et al. | 422/89 |
| 5,477,046 A | | 12/1995 | Dietrich et al. | 250/288 |
| 5,521,381 A | * | 5/1996 | Gregg et al. | 250/288 |
| 5,525,799 A | * | 6/1996 | Andresen et al. | 250/288 |
| 5,611,846 A | * | 3/1997 | Overton et al. | 96/102 |
| 5,686,655 A | * | 11/1997 | Itoi | 73/23.37 |
| 5,837,883 A | * | 11/1998 | Itoi | 73/23.37 |
| 5,959,297 A | * | 9/1999 | Weinberg et al. | 250/288 |

\* cited by examiner

*Primary Examiner*—Hezron Williams
*Assistant Examiner*—Charles D. Garber
(74) *Attorney, Agent, or Firm*—Alan H. Thompson; Ann M. Lee

(57) ABSTRACT

A portable, lightweight (approximately 25 kg) gas chromatograph mass spectrometer, including the entire vacuum system, can perform qualitative and quantitative analyses of all sample types in the field. The GC/MS has a conveniently configured layout of components for ease of serviceability and maintenance. The GC/MS system can be transported under operating or near-operating conditions (i.e., under vacuum and at elevated temperature) to reduce the downtime before samples can be analyzed on-site.

38 Claims, 3 Drawing Sheets

PORTABLE GAS CHROMATOGRAPH MASS SPECTROMETER FOR ON-SITE CHEMICAL ANALYSES

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates to a portable gas chromatograph mass spectrometer particularly suited for chemical analyses in the field.

2. Description of Related Art

For safety reasons, it is often critical to quickly determine, to a high degree of accuracy, the level and type of contamination from unknown chemicals in certain environmental, industrial, civilian, or military settings. Although there are numerous methods of quantitative analysis, the instrumentation is typically cumbersome and not routinely field-deployable for on-site sample analysis. In particular, a gas chromatograph mass spectrometer (GC/MS) is a powerful tool that is routinely used in most analytical labs worldwide for the characterization and quantitative determination of known and unknown chemical species. A GC/MS carries out a mass spectrometric analysis for each constituent of the sample separated by the GC column, providing highly sensitive and accurate identification of each constituent.

However, most commercial GC/MS systems are non-portable, laboratory-based systems, or are only transportable when the necessary external support equipment (gas supply, vacuum system, computer, etc.) is also transported. In addition, most of the commercial systems are for analysis of volatile samples. Examples of GC/MS systems can be found in U.S. Pat. Nos. 5,686,655, 5,837,883, 5,313,061, and 5,083,450. The '655 patent to Itoi shows a system in which the GC unit and the MS unit are mounted such that the system occupies less table-top or floor space. The '061 patent describes a GC/MS system that has an internal volume of less than a cubic yard.

A need exists for a relatively lightweight, portable instrument that is a cost-effective and efficient means for analyzing on-site unknown chemical samples in a variety of emergency and non-emergency circumstances. To this end, a portable GC/MS system was designed and developed at Lawrence Livermore National Laboratory and is described in U.S. Pat. No. 5,525,799 to Andresen et al., which is hereby incorporated by reference. This system has been further improved to provide a portable, lighter, more compact, field reliable/serviceable GC/MS system for rapid on-site analysis of chemical unknowns.

SUMMARY OF THE INVENTION

The present invention is an improved portable gas chromatograph mass spectrometer (GC/MS). The object of this invention is to provide a relatively light-weight (approximately 55 lbs. or 25 kg) GC/MS unit, including the vacuum pumping system, that can perform qualitative and quantitative analyses of all sample types, including volatiles, liquids, and complex samples such as semi-volatiles, sludges, charred organics, and hazardous organics. The hand portable GC/MS system integrates a gas chromatograph, a mass spectrometer with a mass selective detector, several vacuum pumps, and an electronic control system with dedicated software. The entire GC/MS system is conveniently housed and configured in one enclosure, where the various components are modular and accessible for maintenance and serviceability.

A variety of hardware features have been incorporated into this portable GC/MS system, including a fail safe electronic system for automatic shutdown of the MS in the event of vacuum loss or run-away heaters; self-contained carrier gas supply for extending sample analyses, handling larger capillary GC columns, and prolonging the purge times; an auxiliary carrier gas line in the manifold system for optional hook-up to an external gas source; pump-out capability of the carrier gas line to conserve the use of carrier gas for sample analyses; and a GC injector with a small sample reservoir to enhance chromatography and compound detection limits. There is computer control for power time sharing between the heaters and the vacuum pump(s), resulting in lower peak power requirements.

One embodiment of the invention includes a "stand-by mode" capability, in which vacuum pumps and heaters maintain the MS at operating or near-operating pressure and temperature conditions during transport of the GC/MS unit to the site of sample analyses. This innovative feature permits the GC/MS system to be transported under operating or near-operating conditions so as to eliminate or reduce the downtime (or ramp-up time) before samples can be analyzed on-site. The unit's low power consumption enables the GC/MS to operate from a vehicle's cigarette lighter jack via an inverter.

This portable GC/MS can be applied in many fields, including forensics and law enforcement, chemical weapons monitoring, hazardous materials monitoring and clean-up, environmental protection, military (i.e., high explosive and propellant analysis), food and drug analyses, international treaty verification work, and scientific field research. This GC/MS technology will be used by industry and the U.S. Government for field analyses and identification of known and unknown chemicals.

The foregoing and other objects, features, and advantages of the invention will become apparent from the following more particular description and as illustrated in the accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a hand portable gas chromatograph mass spectrometer (GC/MS). The instrument is compact, weighs less than about 55 pounds (25 kg), and permits rapid on-site chemical analyses of known and unknown chemicals. All necessary components, including the gas chromatograph and carrier gas system, the mass spectrometer, associated vacuum systems, heaters, electronics and control system, are integrated in one housing. The only auxiliary item is a portable (laptop) control computer. If the unit includes a stand-by mode capability, a temporary power source (i.e., battery) is also needed.

Figure 1A:
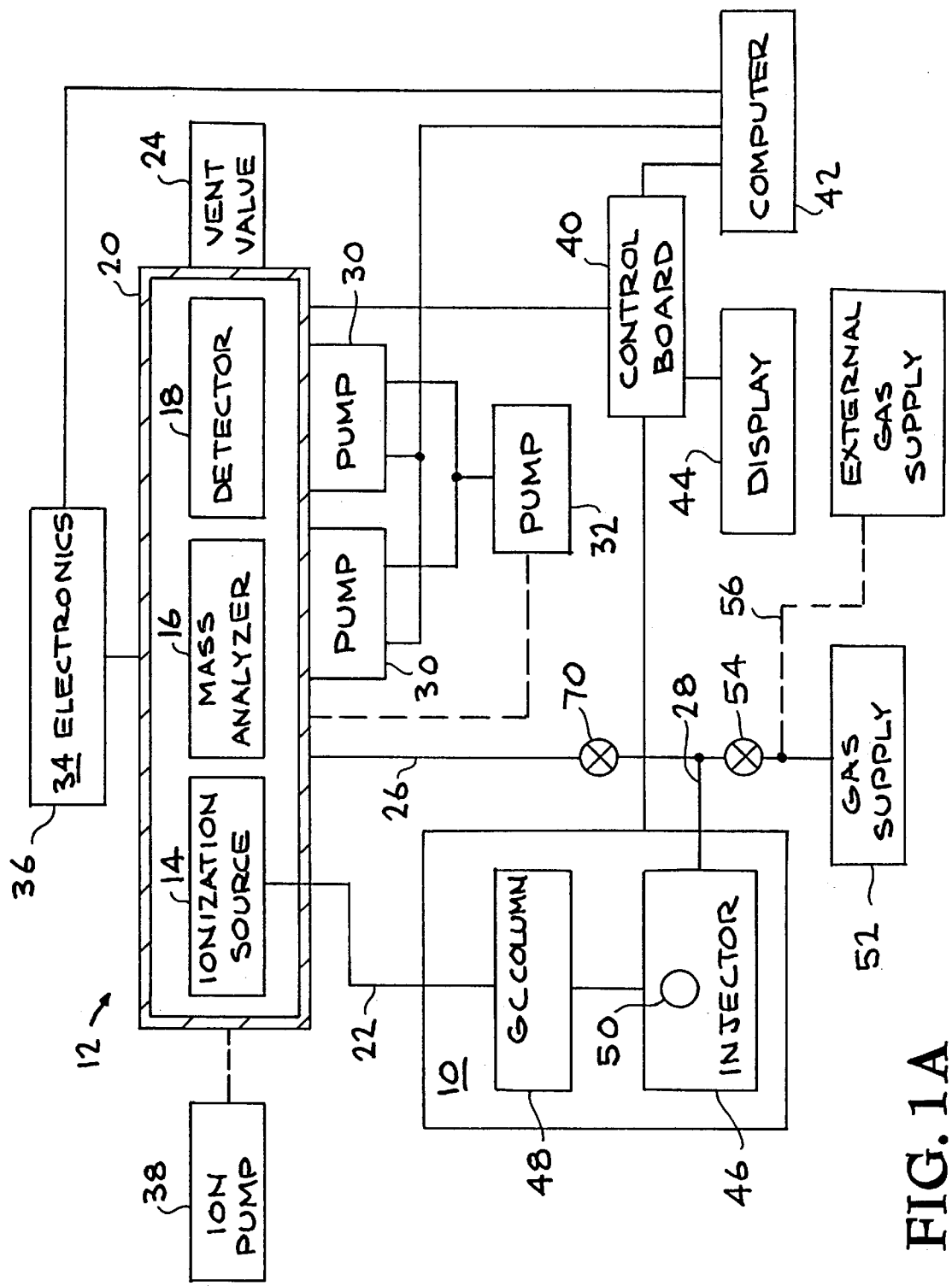
FIG. 1A shows schematically a top view of the gas chromatograph mass spectrometer system according to the present invention.
Figure 1B:
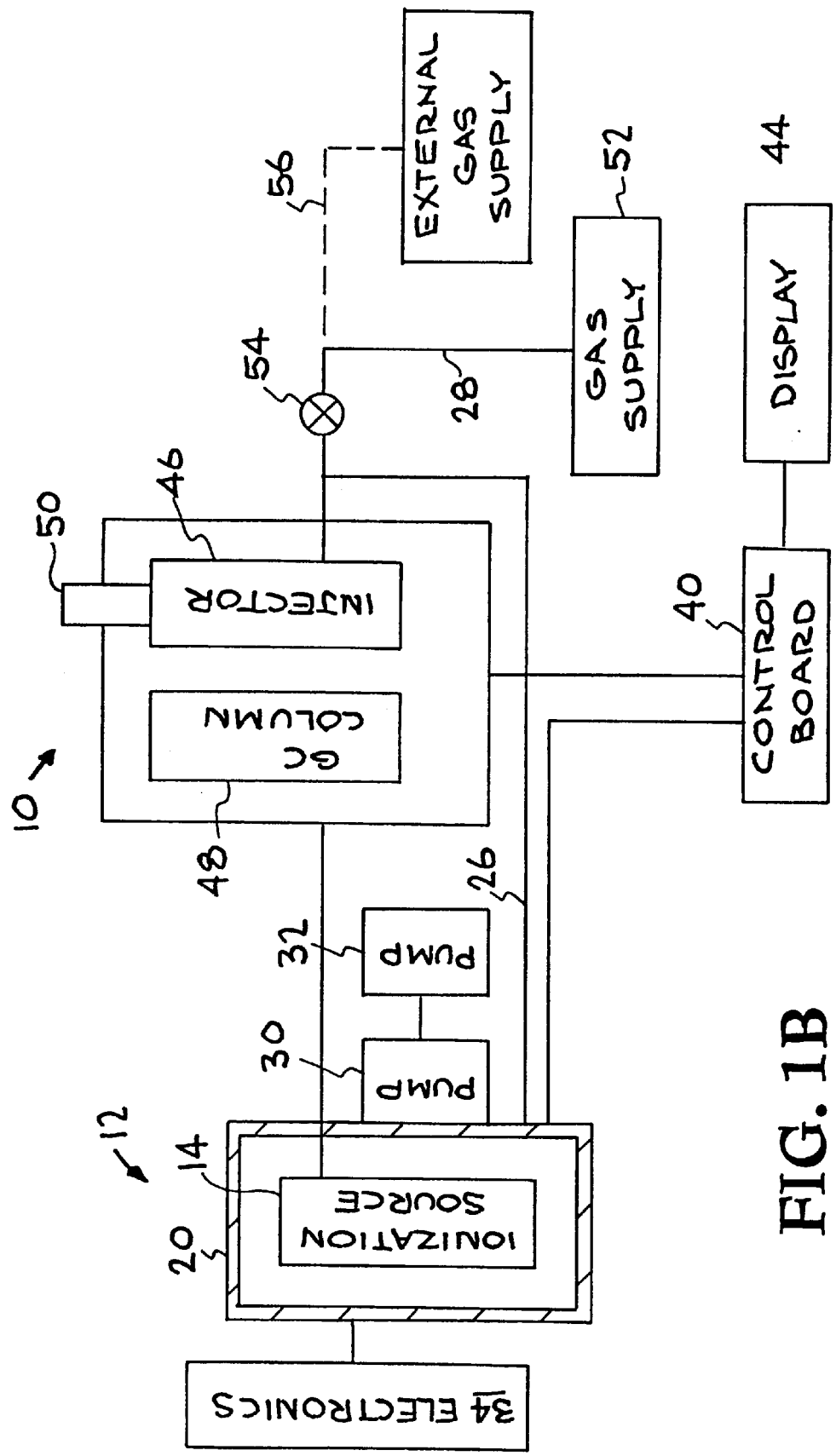
FIG. 1B shows schematically a side view of the gas chromatograph mass spectrometer system according to the present invention.

FIGS. 1A–1B illustrate schematically in top and side views the basic components of the present GC/MS system. These components can be arranged in different ways to occupy the unit's volume; FIGS 1A–1B show one possible configuration. The internal volume of the system is less than four cubic feet or one-tenth of a cubic meter. The dimensions of a system that has been built are about 24 in. length×15 in. width×16 in. height (60 cm×38 cm×40 cm), or an internal volume of about 3.3 ft$^3$ (about 0.09 m$^3$). The dimensions can be reduced even further (<3 ft$^3$) by a more compact layout of the various components.

In FIGS. 1A–1B, the gas chromatograph (GC) is generally indicated at 10, and the mass spectrometer (MS) is generally indicated at 12. The MS 12 includes an ionization source 14, a mass analyzer 16, and a detector 18 housed in a vacuum chamber 20. The GC/MS is a mass selective detector quadrupole and is equivalent in performance, reliability and serviceability to laboratory-based quadrupole GC/MS systems. A commercially available quadrupole mass spectrometer is made by Hewlett-Packard (HP 5973 MSD), which has mainframe specifications that include a GC interface, electron impact ion source, gold plated monolithic quartz hyperbolic quadrupole mass filter, electron multiplier detector, power supply, drive electronics, and analyzer vacuum system. The resolution of the MS is at least 0.1 AMU, and the mass range is at least 800 AMU.

The MS vacuum chamber 20 has at least seven ports for various connections: a full range Pirani/cold cathode pressure gauge (i.e., dynamic range from 760 to 10$^{-9}$ Torr); a calibration valve; a connection or transfer line 22 to the GC; a vent valve 24 to bring the chamber 20 to atmosphere when needed; a pump-out line 26 for the carrier gas line 28; and two connections to turbomolecular drag pumps 30. The dimensions of the vacuum chamber 20 have been reduced to approximately 15½ in.×3½ in.×3 in. (40 cm×10 cm×8 cm; less than 3200 cm$^3$) to reduce the weight and volume of the overall system.

In this embodiment, the MS 12 is operated with a variable heater and two turbomolecular drag pumps 30 backed by an oil-free, shock-mounted diaphragm (roughing) pump 32 (about 3 lbs.). The diaphragm pump 32 may also be connected directly to the MS chamber 20 (as an eighth port). The MS 12 is connected to associated electronics 34 and power supply, which are contained in a housing 36 made with graphite composite material (to decrease unit weight) and EMI shielded on the inside using a copper coating.

Although the GC/MS will operate with a single turbomolecular drag pump, typically two pumps are used, each having a pumping capability of 28 L/sec for hydrogen or 35 L/sec for helium. Each turbomolecular drag pump 30 has a controller, power supply (1.5 lbs.), a fan, and heat dissipation louvers to achieve ventilation. Each turbomolecular pump may also be mounted in aluminum housing to aid in heat dissipation. The entire vacuum pumping system (about 12 lbs.) is thus integrated into the GC/MS system.

In an alternative embodiment with stand-by mode capability, the MS vacuum chamber 20 is also connected to an ion pump 38. Since accurate and sensitive analyses by GC/MS instrumentation depend on sustaining a predetermined vacuum and elevated temperature, one of the advantages of this embodiment is that the operating vacuum and heating requirements for the system are not compromised in the stand-by mode during transportation to another site. This feature eliminates (or at least reduces) the down time (4+ hours) needed to bring the system up to temperature and pump down the vacuum chamber, particularly if a larger vacuum chamber is used. The system has an evacuated and heated mass filter and ion source during transit, maintaining a constant ready state. The heater maintains the MS at the desired operating temperature, and the ion pump maintains a vacuum of about 1×10$^{-7}$ Torr).

In the alternative embodiment, a temporary power source, such as a deep discharge/rechargeable 12V gel cell battery pack, is used to meet the power requirements of the MS source, quadrupole heater, and the ion pump. If the GC/MS instrument is off-loaded to a vehicle on-site, that vehicle's power supply can be used to maintain the stand-by mode during transport to the final sampling destination. For additional energy conservation and lower peak power requirements, the power for the heaters and ion pump may be controlled by computer to allow power time sharing.

Referring back to FIG. 1A, a main control board 40 with associated electronics is connected to the GC 10 and MS 12, as well as to a computer 42 with dedicated hardware and software. The two turbopumps 30 and associated controllers are connected to and operated by the computer 42. The operating system is Hewlett-Packard MS ChemStation and customized software operating under Microsoft Windows NT. The integrated software package provides a complete set of controls for all GC/MS subsystem components such as tuning, heaters, pumps, fans, pressure readings, data acquisition and retrieval, reporting, and library searches. The GC/MS includes a fail-safe electronic system for automatic shutdown in the event of a vacuum loss or runaway heaters.

A conveniently located control and LED display panel 44 has indicator lights and switches which show the operator the on/off status of various components, e.g., vacuum pumps, heaters, valves, etc. The panel 44 provides a visual check for system operations, diagnostics, and permits rapid shutdown.

The power sources for the GC/MS system, which does not include the laptop computer or printer, are provided below.

| 110VAC: | |
|---|---|
| HP5973(MS) + GC Controller | 100 Watt |
| Heaters: | |
| Transfer Line | 50 Watt |
| H$_2$ Bottle | 50 Watt |
| Injection | 50 Watt |
| GC Column | 300 Watt |
| +24V PS1: (86% Efficiency) | |
| Turbo Pump 1 | 100 Watt |
| Vacuum Gauge | 2 Watt |
| Cooling Fans | 7 Watt |
| +24V PS2: (82% Efficiency) | |
| Turbo Pump 2 | 100 Watt |
| Roughing Pump | 35 Watt |

The GC 10 includes an injector 46 with programmable heating up to 325° C., a commercial capillary GC column 48 that can be programmably heated within the GC 10 up to 325° C., and a transfer line 22 with programmable heating up to 325° C. (to prevent condensation). The sample is introduced into the injector 46 through an injector port 50, and then is swept into the capillary GC column 48. The GC column 48 is heated via heated air circulation, with a louvered vent and fan system to dissipate the heat. The column 48 is connected to a heated (and/or insulated) transfer line 22, and the sample passes out of the column 48, through the transfer line 22, and into ionization source 14 of the mass analyzer 16. As shown in FIG. 1B, the injector 46 can be vertically mounted for potential auto-sampler use.

The injector 46 is connected to a self-contained, internal carrier gas supply 52 via a carrier gas line 28 with a valve 54. Pressure transducers monitor the gas pressure in the carrier gas line 28 and the injector 46, and this information is sent to the control board 40. The carrier gas is typically hydrogen ($H_2$) stored in hydride gas cylinders, and a regulator regulates the gas flow. The gas cylinders extend the number of sample analyses and the purges between samples, as well as permit larger capillary GC columns if needed. Two cylinders (20 std. liters each) can provide at least three weeks of continuous sample analysis operations (e.g., 150 samples, calculated at 1 mL/min flow rate and 50 mL/min purge for 15 minutes). As larger volume cylinders (70 std. liters) become commercially available (making replacement less frequent), the number of continuous analyses will increase. An auxiliary carrier gas line 56 in the manifold system may be included for optional hook-up to an external gas supply (e.g., He or $H_2$).

Another feature of the present system is the unique pump-out capability of the carrier gas line 28 between the injector 46 and the carrier gas supply 52. This pump-out capability conserves carrier gas for analysis and eliminates the time necessary to run gas through the GC column. The carrier gas line 28 may be connected via a pump-out line 26 and valve 70 to the vacuum chamber 20 for purging the injector 46 and capillary GC column 48.

Figure 2:
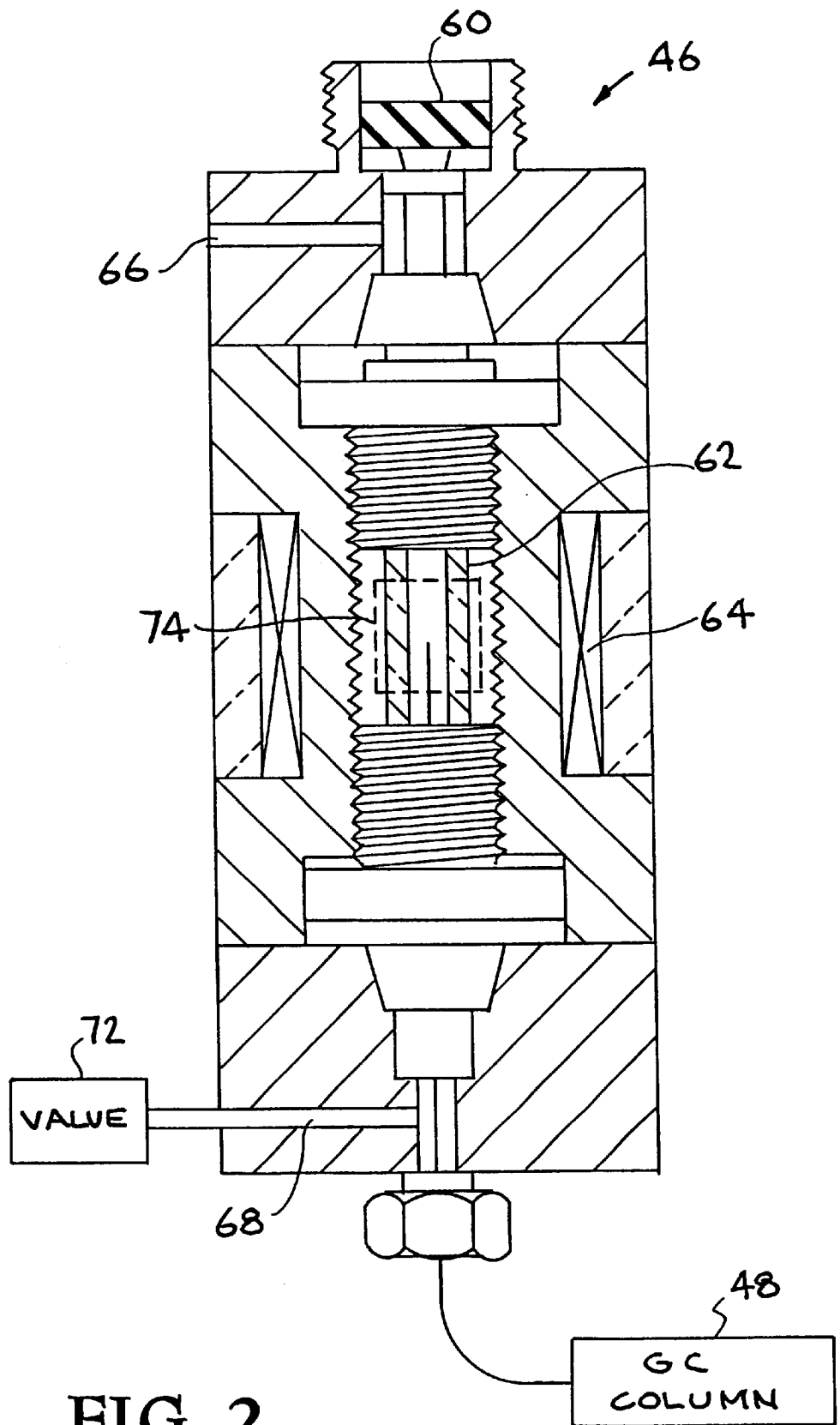
FIG. 2 shows the gas chromatography injector according to the present invention.

FIG. 2 shows an embodiment of a specially designed injector 46. The sample may be introduced by a microsyringe through a rubber septum 60 into a small quartz injection sleeve 62 or liner or tube (e.g., 0.075 inch inner diameter, 3 in. length, 0.013 $in^3$ or 0.22 $cm^3$). The sleeve 62 contains the sample and is surrounded by a variable heater 64 with an insulated jacket, which heats the sleeve 62 to a temperature above the boiling points of all possible components in the sample (e.g., >300° C.). A liquid sample instantly vaporizes and is swept through the sleeve 62 by the flow of carrier gas.

The carrier gas is introduced into the injector 46 through a gas-in port 66 at the top of the sleeve 62. The gas flow carries the vaporized sample through the injector 46 to the GC column 48. The injector 46 has a gas-out port 68 at the bottom (or other end) of the sleeve 62, which leads to a solenoid valve 72 that is computer control activated when purging the injector 46 between samples with the carrier gas or to split flow operations with the carrier gas. The flow of the carrier gas may also be run in the reverse direction with the same analytical results, i.e., the gas-in port is 68 and the gas-out port is 66 at the top of the injector 46, leading to a solenoid valve. Another design feature of the injector 46 is a sight glass 74 to permit visual inspection of the sleeve 62 and glass wool plug in the sleeve to determine when replacement is needed.

The vaporized sample is contained inside a small inner diameter quartz sleeve 62, which provides at least two advantages. This design yields a lower dead volume, which effectively concentrates the sample. Small, concentrated samples are preferred to improve peak shape. In addition, the small tube requires less gas to purge between samples. The injection port is thus designed to facilitate and enhance superior chromatography and compound detection limits. Nevertheless, if injector 46 is not used, the design of the GC in the present system will also accommodate commercial injection ports.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

What is claimed is:

1. A portable gas chromatograph mass spectrometer system for on-site chemical analyses of samples, comprising:
   a mass spectrometer;
   a chamber for containing the mass spectrometer;
   a vacuum system connected to the chamber for maintaining a vacuum in the chamber, said vacuum system comprising one or more turbomolecular drag pumps;
   a gas chromatograph;
   an internal carrier gas supply connected to the gas chromatograph; and
   an electronic control system connected to the mass spectrometer and the gas chromatograph;
   wherein the system has a weight of about 25 kilograms or less.

2. The system as recited in claim 1, wherein the system has a volume of about four cubic feet (0.1 cubic meters) or less.

3. The system as recited in claim 1, wherein the vacuum system further comprises a roughing pump to back up the turbomolecular pump.

4. The system as recited in claim 1, wherein the vacuum system further comprises an ion pump for maintaining a vacuum in the chamber during transport of the system while the system is not analyzing samples.

5. The system as recited in claim 1, wherein the vacuum system comprises at least two turbomolecular drag pumps.

6. The system as recited in claim 1, wherein the gas chromatograph comprises an injector for receiving a sample to be analyzed, wherein the injector comprises an injection sleeve for containing the sample when vaporized and is connected via a carrier gas line to the carrier gas supply, whereby the carrier gas flows through the sleeve.

7. The system as recited in claim 6, wherein the injector is connected via a line and a valve to the vacuum chamber.

8. The system as recited in claim 6, wherein the internal carrier gas supply comprises a gas cylinder.

9. The system as recited in claim 6, further comprising a line for connecting the injector to an external carrier gas supply.

10. The system as recited in claim 6, wherein the sleeve has a volume of about 0.2 $cm^3$ or less.

11. The system as recited in claim 6, further comprising a sight glass for visual inspection of the injection sleeve.

12. The system as recited in claim 1, wherein the vacuum chamber has a volume of about 3200 $cm^3$ or less.

13. The system as recited in claim 1, further comprising a heater connected to the mass spectrometer for maintaining an elevated temperature during transport of the system while the system is not analyzing samples.

14. The system as recited in claim 1, wherein the vacuum system comprises an ion pump for maintaining a vacuum in the chamber during transport of the system while the system is not analyzing samples, and further comprising a heater connected to the mass spectrometer for maintaining an elevated temperature during transport, and further comprising means to connect the ion pump and the heater to an external temporary power source.

15. The system as recited in claim 14, wherein the heater maintains the mass spectrometer at about a selected operating temperature.

16. The system as recited in claim 1, further comprising a control and display panel.

17. The system as recited in claim 1, wherein the system has a power consumption of less than about 550 watts peak power load from cold start-up.

18. The system as recited in claim 1, wherein the system has a power consumption of less than about 250 watts during operation.

19. The system as recited in claim 1, wherein the mass spectrometer has a resolution of less than about 0.1 AMU.

20. A portable gas chromatograph mass spectrometer system for on-site chemical analyses of samples, comprising:

a mass spectrometer;

a chamber for containing the mass spectrometer;

a vacuum system connected to the chamber for maintaining a vacuum in the chamber, said vacuum system comprising one or more turbomolecular drag pumps;

a gas chromatograph;

an internal carrier gas supply connected to the gas chromatograph; and an electronic control system connected to the mass spectrometer and the gas chromatograph;

wherein the system is enclosed within one housing.

21. The system as recited in claim 20, wherein the system has a volume of about four cubic feet (0.1 cubic meters) or less.

22. The system as recited in claim 20, wherein the vacuum system further comprises a roughing pump to back up the turbomolecular pump.

23. The system as recited in claim 20, wherein the vacuum system further comprises an ion pump for maintaining a vacuum in the chamber during transport of the system while the system is not analyzing samples.

24. The system as recited in claim 20, wherein the vacuum system comprises at least two turbomolecular drag pumps.

25. The system as recited in claim 20, wherein the gas chromatograph comprises an injector for receiving a sample to be analyzed, wherein the injector comprises an injection sleeve for containing the sample when vaporized and is connected via a carrier gas line to the carrier gas supply, whereby the carrier gas flows through the sleeve.

26. The system as recited in claim 25, wherein the injector is connected via a line and a valve to the vacuum chamber.

27. The system as recited in claim 25, wherein the internal carrier gas supply comprises a gas cylinder.

28. The system as recited in claim 25, further comprising a line for connecting the injector to an external carrier gas supply.

29. The system as recited in claim 25, wherein the sleeve has a volume of about 0.2 $cm^3$ or less.

30. The system as recited in claim 25, further comprising a sight glass for visual inspection of the injection sleeve.

31. The system as recited in claim 20, wherein the vacuum chamber has a volume of about 3200 $cm^3$ or less.

32. The system as recited in claim 20, further comprising a heater connected to the mass spectrometer for maintaining an elevated temperature during transport of the system while the system is not analyzing samples.

33. The system as recited in claim 20, wherein the vacuum system comprises an ion pump for maintaining a vacuum in the chamber during transport of the system while the system is not analyzing samples, and further comprising a heater connected to the mass spectrometer for maintaining an elevated temperature during transport, and further comprising means to connect the ion pump and the heater to an external temporary power source.

34. The system as recited in claim 33, wherein the heater maintains the mass spectrometer at about a selected operating temperature.

35. The system as recited in claim 20, further comprising a control and display panel.

36. The system as recited in claim 20, wherein the system has a power consumption of less than about 550 watts peak power load from cold start-up.

37. The system as recited in claim 20, wherein the system has a power consumption of less than about 250 watts during operation.

38. The system as recited in claim 20, wherein the mass spectrometer has a resolution of less than about 0.1 AMU.

* * * * *

UNITED STATES PATENT AND TRADEMARK OFFICE
Certificate

Patent No. 6,351,983 B1

Patented: March 5, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jeffrey S. Haas, San Ramon, CA; John F. Bushman, Oakley, CA; Douglas E. Howard, Livermore, CA; James L. Wong, Livermore, CA; Joel D. Eckels, Livermore, CA; and Brian D. Andresen, Livermore, CA.

Signed and Sealed this Fifteenth Day of March 2005.

HEZRON E. WILLIAMS
*Supervisory Patent Examiner*
Art Unit 2856